(12) United States Patent
Knickerbocker et al.

(10) Patent No.: US 10,621,885 B2
(45) Date of Patent: Apr. 14, 2020

(54) WEARABLE SENSOR MONITORING AND DATA ANALYSIS

(71) Applicant: International Business Machines Corporation, Armonk, NY (US)

(72) Inventors: John U. Knickerbocker, Monroe, NY (US); Shriya Kumar, White Plains, NY (US); Kang-Wook Lee, Yorktown Heights, NY (US); Minhua Lu, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 984 days.

(21) Appl. No.: 14/985,485

(22) Filed: Dec. 31, 2015

(65) Prior Publication Data
US 2017/0189751 A1    Jul. 6, 2017

(51) Int. Cl.
*G09B 19/00* (2006.01)
*A61B 5/11* (2006.01)
*G16H 20/30* (2018.01)
*A61B 5/00* (2006.01)
*G16H 40/67* (2018.01)
*G16H 40/63* (2018.01)

(52) U.S. Cl.
CPC ........ *G09B 19/0038* (2013.01); *A61B 5/0022* (2013.01); *A61B 5/1114* (2013.01); *G09B 19/003* (2013.01); *G16H 20/30* (2018.01); *G16H 40/63* (2018.01); *G16H 40/67* (2018.01); *A61B 2560/0242* (2013.01)

(58) Field of Classification Search
None
See application file for complete search history.

(56) References Cited

U.S. PATENT DOCUMENTS

2006/0189852 A1* 8/2006 Greenwald .......... A61B 5/0002
                                                      600/300
2007/0130893 A1* 6/2007 Davies ................. A01K 11/008
                                                      54/1

(Continued)

OTHER PUBLICATIONS

Nuviun, "Sensors and Wearables", Sep. 7, 2015, website last visited on Dec. 30, 2015, pp. 1-4.

(Continued)

*Primary Examiner* — Nathan Hillery
(74) *Attorney, Agent, or Firm* — Fleit Intellectual Property Law; Jeffrey N. Giunta

(57) ABSTRACT

Systems and methods for monitoring body mounted/implanted sensors in combination with environmental sensors and sensors attached to person's medical/sports equipment. Data indicating a plurality of measured quantities associated with movement of a person at a time point is received. Each measured quantity within the plurality of measured quantities having been determined by a respective sensor attached to a respective location on the person or the person's environment or the person's medical/sports equipment. At least one characteristic of the person associated with the time point is determined based on analyzing the plurality of measured quantities. The at least one characteristic is stored. Recommendations for the person are determined based upon the characteristics, and a report comprising the recommendations is provided.

16 Claims, 8 Drawing Sheets

(56) References Cited

U.S. PATENT DOCUMENTS

| | | | | |
|---|---|---|---|---|
| 2010/0204616 A1* | 8/2010 | Shears | ............... | A61B 5/1127 600/595 |
| 2013/0002435 A1* | 1/2013 | Utter, II | ............ | A61B 5/0022 340/575 |
| 2013/0176142 A1* | 7/2013 | Drysdale | ............... | G06F 3/011 340/870.02 |
| 2013/0211858 A1* | 8/2013 | Ohnemus | .............. | G16H 10/60 705/3 |
| 2014/0247142 A1* | 9/2014 | Proud | ............... | A61B 5/0022 340/870.02 |
| 2015/0318015 A1* | 11/2015 | Bose | .................... | H04N 7/188 386/248 |
| 2016/0038083 A1* | 2/2016 | Ding | .................. | A61B 5/6804 600/388 |
| 2017/0006950 A1* | 1/2017 | Miller, II | .............. | A42B 3/046 |

OTHER PUBLICATIONS

Zepp, "Zepp Baseball User Guide", last updated on Apr. 30, 2015, pp. 1-24.
Palermo, E., "Zepp Golf Swing Analyzer: Sports Tracker Review", Dec. 2, 2014, pp. 1-8.

* cited by examiner

WEARABLE SENSOR MONITORING AND DATA ANALYSIS

BACKGROUND

The present disclosure generally relates to the field of monitoring wearable sensors, and more particularly to collecting, storing and analyzing data obtained from sensors on a person and from other sources.

Monitoring parameters associated with a person's health, fitness and/or level of physical performance in various physical activities can be beneficial in many ways. For example, people involved in various levels of routine exercise can monitor the progress of their development and determine possible changes or enhancements to their routines. Persons active in a particular sport, whether at a casual level or up through a professional level, can monitor the development of their performance in various activities related to that sport. Also, monitoring health and fitness related characteristics of a person can be helpful when the person is recovering from surgery or an injury. Often, monitoring quantities associated with a person's heath, fitness, and/or level of performance can be one or more of inconvenient, costly, or otherwise challenging.

BRIEF SUMMARY

A method on a processor includes receiving data indicating a plurality of measured quantities associated with movement of a person at a time point. Each measured quantity within the plurality of measured quantities having been determined by a respective sensor physically coupled to the person at a respective location on the person. The method also includes receiving environmental data indicting environmental quantities associated with the person. At least one characteristic of the person associated with the time point based on analyzing the plurality of measured quantities in combination with the environmental data is determined. The at least one characteristic is stored. The method further includes determining at least one recommendation for the person based upon the characteristics; and providing a report comprising the at least one recommendation.

A method on a device includes measuring a plurality of quantities of a person where each quantity within the plurality of quantities is measured at a respective time by a respective sensor physically coupled to the person at a respective location of the person. The method also includes receiving environmental data indicting environmental quantities associated with the person. At least one characteristic based upon processing the plurality of quantities and the environmental data is determined. The method further includes sending, based upon the determining or the measuring, the plurality of quantities, the environmental data, and the at least one characteristic to a remote processor.

A data processor includes a data receiver that, when operating, receives data indicating a plurality of measured quantities associated with movement of a person at a time point where each measure quantity within the plurality of measured quantities is determined by a respective sensor physically coupled to the person at a respective location on the person. The data receiver further receives environmental data indicting environmental quantities associated with the person. The data processor further includes a data analyzer that, when operating, determines at least one characteristic of the person associated with the time point based on analyzing the plurality of measured quantities in combination with the environmental data; stores the at least one characteristic; determines recommendations for the person based upon the characteristics; and provides a report comprising the recommendations.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various examples and to explain various principles and advantages all in accordance with the present disclosure, in which.

DETAILED DESCRIPTION

Figure 1:
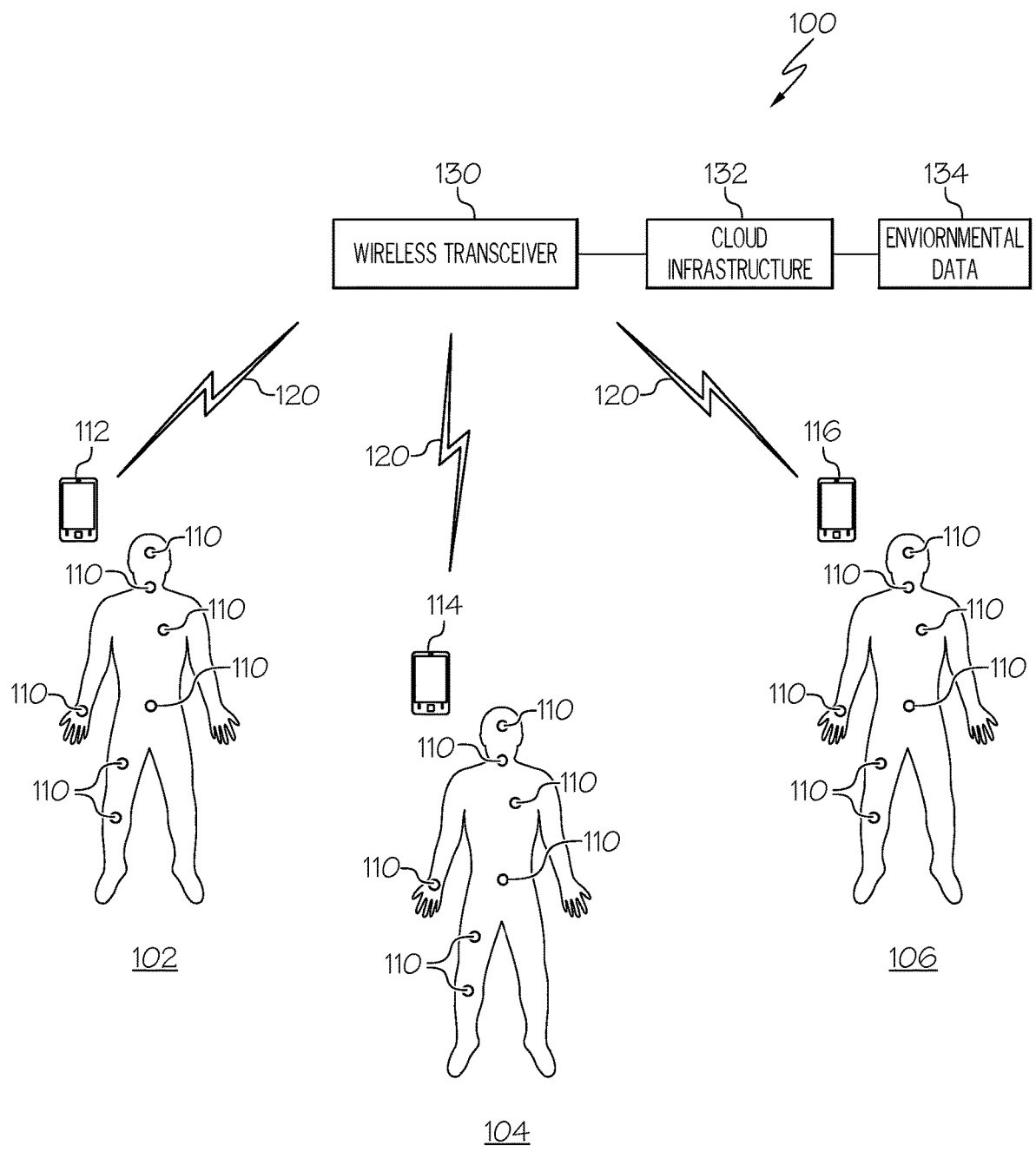
FIG. 1 illustrates a multiple person monitoring environment, according to an example.

The below described system and method operate to provide integrated wearable electronics that make up a system of sensors and healthcare monitors that are coupled with one or more interactive sensors, micro-controllers, energy source, or memory storage to provide an integrated and convenient physical monitoring system for a person or animal. In one example, micro-subsystems that include sensors can be skin-wearable, placed within wearable articles such as clothing, shoes/sneakers or equivalent, socks, hat, gloves, scarfs, wearable smart tags, watches, articles of jewelry, or the like, are disposed around a person, implanted in the person or otherwise attached to the person. These sensors are able to measure quantities associated with the person. In some examples, all, some, part, or combinations, of the microsystems that include sensors are able to be implanted at various locations of the person. In the following discussion, a sensor is said to be physically coupled to a person if that sensor is attached to the person in any way. Examples of physically coupling a sensor to a person include, but are not limited to, placing a sensor in any type of skin wearable article that is worn by the person, placing a sensor in or on any article worn by or attached to the person, by being implanted into the person in any manner, by any other physical coupling, or by combinations of these. Sensors in some examples are said to be physically coupled to the person at a respective location of the person by being physically coupled to a location, such as at a joint or other location, on or near the person's body.

The sensors that are near a person or physically coupled to the person are able to measure quantities that are be associated with one or more of movement of the person, physiological measurements of the person, biometric measurements used to identify the person, environmental information for the person, data from equipment held by or otherwise used by the person, any suitable measurement, or combinations of these. These sensors in an example are able to interact with a smart phone or other device that communicates with and collects the measurements made by these sensors. In an example, the smart phone or other device is able to provide some processing of the quantities measured by these sensors in order to determine information to present to the person or other interested and authorized individuals. The smart phone or other device is further able to provide communications with other systems. In an example, the smart phone or other device is a communications device that provides data communications to a cloud based computing infrastructure or other server based data processing. In an example, the cloud based infrastructure or other server based data processing performs data analytics and determines information, such as characterizations of measured quantities of physical measurements of the person, suggestions regarding physical activity, feedback, other information related, based on, or derived from the quantities measured by the sensors, or combination of these.

In addition to receiving, collecting and analyzing quantities measured by sensors physically coupled to the person, data characterizing environmental conditions at or near the person is also collected in association with the data provided by sensors characterizing the person's movements. For example, such environmental quantities are able to include, but are not limited to, air temperature, humidity, wind speed, ultraviolet (UV) light exposure, concentrations of particulate matter in the air, other quantities, or combinations of these. Environmental quantities that indicate environmental conditions near the person in some examples are able to be obtained from any suitable source. For example, environmental quantities are able to be measured by sensors physically coupled to the person or that are located near the person. An electronic device, such as a smart phone or other electronic device, that receives data from sensors physically coupled to the person are also able to include sensors to measure environmental quantities. Environmental quantities may also be measured by any sensor suitably close to the person. Data indicating environmental conditions are also able to be received from any other source such as publicly available weather, air quality, other environmental condition data, or combinations of these. Environmental quantities indicating environmental conditions are able to be obtained from any one or more of these sources or any other suitable source.

These electronic sensors and one or more communication devices in an example form a system that provides personalized monitoring of a person or animal. Animals for which such monitoring apparatuses can be used include, but are not limited to, pets, racing animals, draft animals, animals involved in performing show routines or other demonstrations, other animals whose physical performance is of interest, or any other animal. In the following discussion, any reference to person is intended to include the body of any type of animal, including humans and other animals such as those listed above. These systems are able to provide one or more of multiple functions, data transmission, data storage, or interaction with one or more various processors that are able to be either local, remote, or both. These systems are able to provide information related to health and/or wellness, are able to record body functions and environmental factors including, but not limited to, temperature, hydration, pulse, blood pressure, movements, rate of movements and location of movements of body relative to one another and the person's environment. These systems are further able to sense muscle changes, fatigue, $O_2$ level in the person's blood, or combinations of these.

The measured characteristics and relative movements of different parts of the person are able to be compared to recorded characteristics or movements of that same person or of others. For example, the recorded or determined movements and other characteristics of a person are able to be compared to prior characteristics or movements that were measured at different times of the person's training or development to characterize the training or development of the person. Further, recorded characteristics or movements are able to be compared to measured or determined characteristics or movements for others, such as professional athletes, trainers, or any other person. Such comparisons to that person's past performance or to characteristics of others is able to be a basis for providing feedback, recommendations, other further information, or combinations of these, for the benefit of the person, pet, or to a caregiver.

Examples of applications for such a system include, but are not limited to, monitoring or characterizing a person's wellness or condition, determining energy consumed by the person, determining hydration of the person, dehydration of the person, other relevant measurements, or combinations of these. Such systems are able to aid, for example, a personal trainer or rehabilitation specialist for activities such as golf or tennis, general personal fitness, recovery from surgery or injury, recovery from or treatment of a medical condition, recording and tracking the person's improvement and history of development, or any other application.

In an example, the measured data and determined characteristics, trends, recommendations, other information, or combinations of these, are able to be encrypted by any part of the system. For example, one or more sensors are able to encrypt measured data prior to sending the data to a device that is physically coupled to or located near the person. A device physically coupled to or located on the person, such as a smart phone or other personal electronic device, is also able to encrypt data prior to sending that data over a data link to a remote server or cloud based infrastructure. The server or cloud based infrastructure is also able to encrypt data that it processes, or that is produced by processing data received from sensors on a person, in order to provide security for the recorded personal information, determined characteristics, performance tracking, recording and to restrict access to that data to only authorized persons.

Various types of sensors and electronics can be used and combined into a monitoring system. Examples include using electronics that are wearable on a person's skin, embedded in one or more types of clothing or worn articles such as socks, shoes, headbands, or other articles. Motion sensors can determine positions of body parts to which they are physically coupled, and sensors or data processing can track the relative positions of two or more sensors with respect to one another. For example, multiple sensors that determine quantities such as position, speed, velocity, other quantities, or combinations of these can each be placed at locations on a person such as the front of each of a person's foot, the back of each of the person's foot, each of the person's ankles, each of the person's knees, at each of one or more positions on the person's hips, at each of one or more positions on the person's shoulders, at each of one or more positions on the person's elbows, at each of one or more positions on the person's wrists, at each of one or more positions on the person's hands, at each of one or more positions on the person's head, or any one of or combinations of these. In an example, sensors determining quantities associated with sensor location, sensor motion, sensor velocity, other quantities, or combinations of these, are able to be placed at or near various joint locations of the person's or animal's body. For example, sensors such as electrocardiogram (ECG) sensors to measure heart rate, electromyography sensors to measure muscle activity, pulse wave sensors to measure blood pressure, heart sound sensors to study heart activity, electrochemical sensors that detect glucose levels from tear and sweat, electrolyte levels from sweat, lactic acid levels from sweat, any other such sensors, or combinations of these are able to be used to determine and report various data that indicates measured quantities for the person.

Sensors that determine pressure applied to the sensor can detect quantities such as weight and impact when combined with data obtained from sensors determining, for example, one or more of motion, direction of movement, sensor position relative to other sensors, other quantities, or combinations of these. Sensors that monitor electrical resistance can determine ambient humidity, the sweat level on the person, other quantities, or combinations of these. Sensors that capture still images, video images, or both, can be used to detect, for example, movements of ball or equipment such as bats, oars and the like. Determined movements of equipment being used by the person such as balls being caught or thrown, or other equipment can be combined with some or all measurements made by other sensors or with sensors located on, in or otherwise physically coupled to the sports equipment or medical equipment to support improved wellness, healthcare status, quality of an activity, or combinations of these. In general, a piece of equipment being used by a person is able to be any object that is associated with the person's activities. Examples of equipment include, but are not limited to, sports equipment, medical equipment, any other object, or combinations of these. Use of a piece of equipment by a person is able to include, but is not limited to, use of all or part of a piece of equipment. Use of equipment can include, but is not limited to, manipulation of the equipment or object, throwing or swinging of an object associated with the equipment, lifting of an object associated with the equipment, any affect the person may have on an object associated with the equipment, or combinations of these. In general, any measurement or other data characterizing or reflecting movement, use, manipulation of, or other affect on, by the person's activities an object that is all or part of a piece of equipment is referred to as equipment data. Equipment data is able to be measured, determined, otherwise derived, or combinations of these, by sensors within the equipment, sensors external to the equipment, monitoring of the equipment such as by a video capture device, by other techniques, or by combinations of these.

Such measurements, data determinations, or both, are able to be made at any time, such as during exercise, practice, or actual game play. Monitoring such quantities and processing the measured data to determine characteristics for the person is able to be applied to improving performance in various activities, such as personal training for golf, tennis, running, swinging a baseball bat, oar rowing, crew, or any sport. This monitoring, data determination, or both, are also able to aid in monitor progress during treatment for a medical condition or during recovery from a medical procedure such as surgery.

Using multiple sensors that are able to be physically coupled to the person at selected locations of a person's body, as well as potentially on sports equipment or other equipment used by the person such as medial equipment, is able to support monitoring, characterizing, and determination of exercises and training. Combining these measured quantities with environmental data and equipment data offers a more comprehensive set of data to provide to analysis algorithms. Such analysis in some examples is able to be used to support efforts to improve complex physical actions, such as improve a person's posture during sporting activities such as golf by tracking data, communicating that data to a data processor or processors such as in a smart phone, other local device, or other data analysis components such as a cloud based infrastructure. Different levels of analysis in some examples are able to be performed by these various processors in order to determine characteristics and formulate recommendations based on the multiple quantities monitored by the multiple sensors of these comprehensive monitoring systems. The data processor or processors are then able to return such recommendations for further personal training or wellness development, for additional monitoring points to include in the monitoring system during future activities, improvements to exercise, or combinations of these.

In various examples, analysis of the multiple measured quantities and the determination of characteristics are able to be performed by processors located at any suitable location. For example, some processing of measured quantities for a person is able to be performed by processors within a device that is with the person, such as a smart phone or other processor. Some processing is able to be performed by a remote server, such as within a cloud infrastructure, that receives measured quantities, data derived from those measured quantities, or both, from a device with the person.

Data processing used to analyze determined quantities or characteristics is able to include comparisons or other processing based on many diverse sources. For example, a person's measured quantities or characteristics determined by processing or analysis of those determined measured quantities are able to be compared to a set of reference data compiled from any suitable source. For example, deductions or other results are able to be based on comparing measured quantities, or determined characteristics, for a person to any portions of various reference data sets. Examples of reference data sets include large sets of reference data compiled by collecting data from many persons in various demographic groups, from many different types of people participating in similar athletic activities, reference data compiled from any population, or combinations of these. Such data is able to be further presented to skilled persons for analysis, such as to doctors, heath services, other developmental experts, other persons, or combinations of these. These measured quantities and determined characteristics, along with their historical trend as these quantities and characteristics are accumulated over time are able to be used to determine a person's progress and development. Such historical trends are able to assist doctors, health care providers, other wellness professionals, or combinations of these, to determine or detect long term trends in the person's wellness that may benefit from suggested activities.

In an example, such monitoring systems are able to monitor quantities to determine characteristics such as fatigue, dehydration level, wind speed, physical endurance, heart rate, running impact on road, forces on the person's legs and other bones, the person's weight over time versus loss of fluids, body levels of glucose, and body temperature. These data are able to be combined with, for example, one or more types of environmental data, equipment data, other relevant data, or combinations of these. Derived data based on determining trends of quantities and characteristics associated with personal performance and also ambient conditions include aiding a person in identifying conditions when the person does well or when the person has "good days" or "bad days" for speed.

Access to a person's data is able to be controlled by various techniques. In some examples, sensors measure biometric identification data for the person, such as one or more of fingerprints, retina scans, other biometric identification data, or combinations of these. This biometric identification data is able to be used for any purpose, such as to identify the person in association with stored data to ensure that the data for a particular person was measured for that person, used upon attempts to access data to ensure that person attempting access is the person for whom the data was collected, for any other purpose, or for combinations of these.

FIG. 1 illustrates a multiple person monitoring environment 100, according to an example. The multiple person monitoring environment 100 illustrates three persons, a first person 102, a second person 104, and a third person 106. Each of these persons has a wearable monitoring system that includes multiple wearable sensors 110 that are physically coupled to each person. In various examples, the wearable sensors 110 are able to include one or more of sensors that are within or attached to articles worn by the person, sensors that are attached to the person, sensors that are implanted into the person, sensors that are physically coupled to the person in any manner, or combinations of these. In an example, each wearable sensor 110 measures or determines one or more quantities associated with the person's activity. These wearable sensors 110 are physically coupled at various selected points on the person. In some examples, one or more such wearable sensors are able to measure multiple quantities, such as environmental data, video data, other data, or combinations of these.

The multiple wearable sensors 110 on each person in this example each measure one or more quantities and communicate those quantities to a device that is on or near that person. In the illustrated example, the first person 102 has a first device 112, the second person 104 has a second device 114, and the third person 106 has a third device 116. In various examples, the wearable sensors 110 are able to encrypt the data that is communicated to the device in order to protect the information associated with the person wearing the wearable sensor 110. For example, the wearable sensors 110 worn by the first person 102 is able to encrypt data indicating quantities measured by that sensor prior to sending that data to the first device 112.

In some examples, the devices, such as the first device 112, is able to perform some processing of the data received from the wearable sensors 110. For example, such data is able to be converted as may be useful, some characteristics may be determined from the data received from the sensors, any other processing may be performed, or combinations of these. In addition, data received by or generated within the devices is able to be encrypted for further transmission, storage, other uses, or combinations of these. The devices such as the first device 112 is also able to store data, such as data received from the wearable sensor 110 or data generated by processing or other means within the device, or both. The devices in some examples are also able to receive data from various other sources that are either within or external to the device and that data is able to be stored, further processed, presented to the person, otherwise used, or combinations of these.

The devices, such as the first device 112, are able to associate measured quantities with a time point associated with the measurement. The time point associated with a measurement in some examples corresponds to the time at which the measurement was made and indicates the time at which the measured quantity existed in, with, or around the person. In some examples, an indication of the time point is stored with the measured quantities, stored with data derived by processing the measured quantities, stored with other relevant data, or stored with combinations of these.

The devices, such as the first device 112, are able to associate limits for values of quantities measured by the sensors 110, or for characteristics derived from those measured quantities, and monitor those values relative to those limits. In an example, measured quantities that are within the limits associated with those quantities are reported less frequently than values that fall outside those limits. In some examples, conditions associated with the person are derived by processing within the device to determine, for example, an indication that the person is having a heart attack or has fallen. In some examples, the device sends urgent alerts to identified destinations such as emergency responders, caregivers, parents, custodians, other persons or entities, or combinations of these. In some examples, sensors 110, the devices such as the first device 112, or both, are able to have limits associated with their measurements and measured quantities within those limits are able to be defined to be not reported, accumulated and reported with less frequency that values that are not within limits, have a set of processing defined for values that are within limits and another set of processing for values that are not within limits, or any combinations of these.

The devices on each person, such as the first device 112 on the first person 102, are able to exchange data with a cloud infrastructure 132, or other server based processor, over a wireless link 120. The devices communicate data in conjunction with a wireless transceiver 130 with the cloud infrastructure to convey measured quantities determined by the wearable sensors 110, data determined by the device by processing or other means, indications of time points associated with the data, or combinations of these.

In addition to receiving data regarding measured quantities from sensors physically coupled to a person, the cloud infrastructure 132 in some examples receives environmental data from one or more sources indicated as an environmental data source 134. The environmental data obtained from the environmental data source 134 is environmental data such as is described above. The environmental data is able to be collected at any location such that the data is relevant to the person whose data is being analyzed. For example, air temperature, humidity, UV light levels, and other quantities can be presumed to not vary significantly over some distances. Thus, data obtained from a centrally located environmental monitor may be suitable for incorporation into analyses of data for multiple persons in an area, such as on a golf course, athletic field, and the like. In some examples, the area of relevance for environmental data may be extended to include larger areas such as cities, or any defined area. In some examples, the devices, such as the first device 112, located near a person are also able to receive environmental data from any suitable local or remote source and incorporate such environmental data into any analysis performed by a processor within such devices.

Further the devices, such as the first device 112, are able to receive data from the cloud infrastructure, other server based processor, or from any data source. The devices are able to receive data over a wireless link 120 via the illustrated wireless transceiver 130 or any other wireless communications system. The received data is able to be processed, stored, conditioned, displayed to the user, or otherwise utilized by the device. In an example, results determined by processing within the cloud infrastructure 132 based upon quantities measured by the wearable sensors 110 are able to be sent to the devices, such as the first device 112, for any purpose, such as presentation to the first person 102, for storage to allow later review, for any other purpose, or for combinations of these. In some examples, data sent from the device, such as the first device 112, or sent to the device, such as from the cloud infrastructure 132, is able to be encrypted for transmission. The device, such as the first device 112, the cloud infrastructure 132, or both, are also able to encrypt any or all data for storage or other uses in order to protect the data of the person to whom it pertains.

Figure 2:
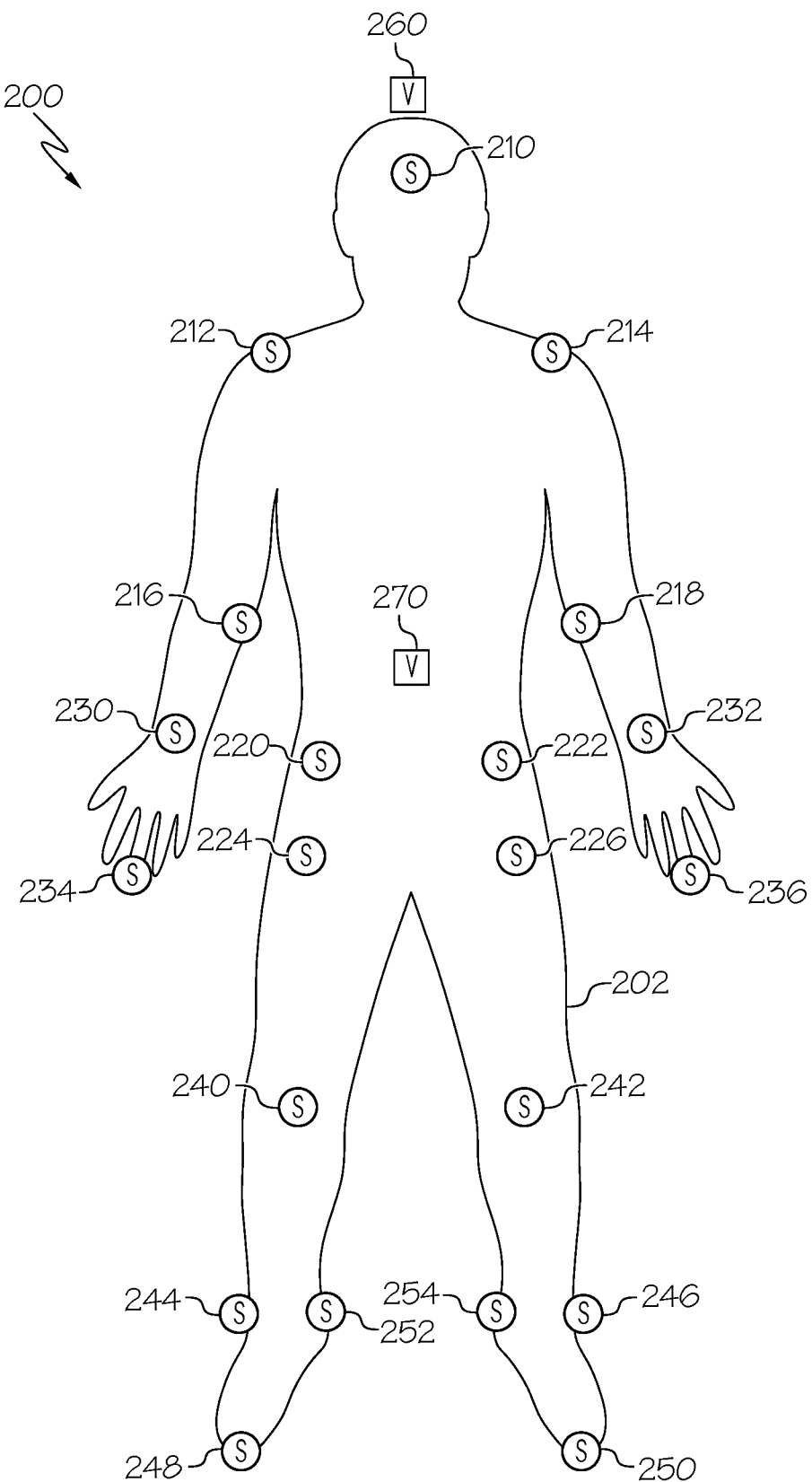
FIG. 2 illustrates a wearable sensor placement configuration, according to an example.

FIG. 2 illustrates a wearable sensor placement configuration 200, according to an example. The wearable sensor placement configuration 200 illustrates an example of locations where sensors, such as the wearable sensors 110 discussed above, are physically coupled to a person 202 to implement monitoring of the person's physical performance. In some examples, some sensors, or parts of sensors, are able to be physically coupled by any suitable technique, such as by attaching to, implanting in, otherwise physically coupling to, or combinations of these, a person at various locations. In the following discussion, a sensor is said to be placed at a location if it is physically coupled in any manner at a place that is in the vicinity of that location.

The wearable sensor placement configuration 200 depicts a head sensor 210 that is placed on a person's head. The head sensor 210 is able to determine quantities associated with the person's head, such as twisting of the neck as well as movements of the upper body in general that cause the head to move. In general, the head sensor 210 is able to measure and determine one or more of the position of the head with respect to a fixed references, the position of the head with respect to other sensors on the person 202, a speed and direction of linear movement of the head, a speed and direction of angular movement of the head, ambient wind speed near the head, other relevant quantities, or combinations of these.

The wearable sensor placement configuration 200 depicts a right shoulder sensor 212 and a left shoulder sensor 214 that are placed on each respective shoulder of the person 202. Placing of these and similar sensors may be by any suitable technique, such as direct attachment, placing in clothes or other wearable items, implanting, other physical coupling, or combinations of these. The right shoulder sensor 212 and the left shoulder sensor 214 are able to determine quantities associated with the person's shoulders, such as twisting of the shoulders as well as movements of the upper body in general that cause the shoulders to move. In general, the right shoulder sensor 212 and the left shoulder sensor 214 are able to measure and determine one or more of the position of each respective shoulder in a fixed frame of references, the relative position of each respective shoulder to the other respective shoulder, the relative position of each respective shoulder with respect to other sensors on the persons 202, a speed and direction of linear movement of the respective shoulders with respect to a fixed reference and to other sensors on the person 202, a speed and direction of angular movement of the respective shoulders with respect to a fixed reference and to other sensors on the person 202, ambient wind speed near the shoulders, other relevant quantities, or combinations of these.

The wearable sensor placement configuration 200 depicts a right elbow sensor 216 and a left elbow sensor 218 that are placed on each respective shoulder of the person 202. The right elbow sensor 216 and the left elbow sensor 218 are able to determine quantities associated with the person's elbows that are similar to those described above as being measured or determined for the person's shoulders by the right shoulder sensor 212 and the left shoulder sensor 214. Similar monitoring and determinations are able to be made by other wearable sensors physically coupled at or near various joints of the person 202 such as the right wrist sensor 230 and left wrist sensor 232, the right hand sensor 234 and left hand sensor 236, a right waist sensor 220 and left waist sensor 222, a right hip sensor 224 and left hip sensor 226, a right knee sensor 240 and left knee sensor 242, and also a right foot sensor 248 and a left foot sensor 250.

In some examples, having multiple sensors are able to be placed near a single joint to monitor quantities to allow more detailed analysis of movements during certain processes. An example in the illustrated wearable sensor placement configuration 200 is the use of a right outer ankle sensor 244 and a right inner ankle sensor 252 along with a left outer ankle sensor 246 and a left inner ankle sensor 254. These multiple sensors worn at different locations near a single joint allow more complex movements to be monitored and recorded for analysis.

Some sensors placed on the person are also able to measure or determine biometric identification data. Such biometric identification data is able to include any data that is able to identify the person. Examples of biometric identification data include, but are not limited to, fingerprints, retina scans, measurements of other unique characteristics, or combinations of these. For example, the right hand sensor 234 is able to be placed on the person's fingertip to measure the person's fingerprint. Characterizations of that fingerprint in this example, are biometric identification data that is able to be, for example, used to uniquely identify the person to verify that measured quantities are stored in association with the correct person, used to limit access to data associated with the person to persons with the same biometric identification data, used for any other purpose, or combinations of these.

In addition to the above described wearable sensors, two visual sensors are shown as being worn by the person 202. A head mounted visual sensor 260 and a torso mounted visual sensor 270 are shown as being mounted on the head and torso, respectively, of the person 202. Such visual sensors are able to capture and record images, videos, or other photographic information in a field of view of those sensors. Such images are able to capture, for example, positions and movements of devices used by the person 202, such as bats or cubs swung by the person 202, balls or other objects thrown by the person 202, any other object, or combinations of these. Further, captured visual images or videos captured by the visual sensors of fixed objects may be used to further characterize movements by the person wearing those visual sensors. In various examples, the visual sensors, such as the head mounted visual sensor 260 or torso mounted visual sensor 270, are able to capture one or more portions of light spectrum, including visual light, infrared light, ultraviolet light, any portion of frequencies of electromagnetic radiation, or any combinations of portions of electromagnetic radiation frequencies.

Figure 3:
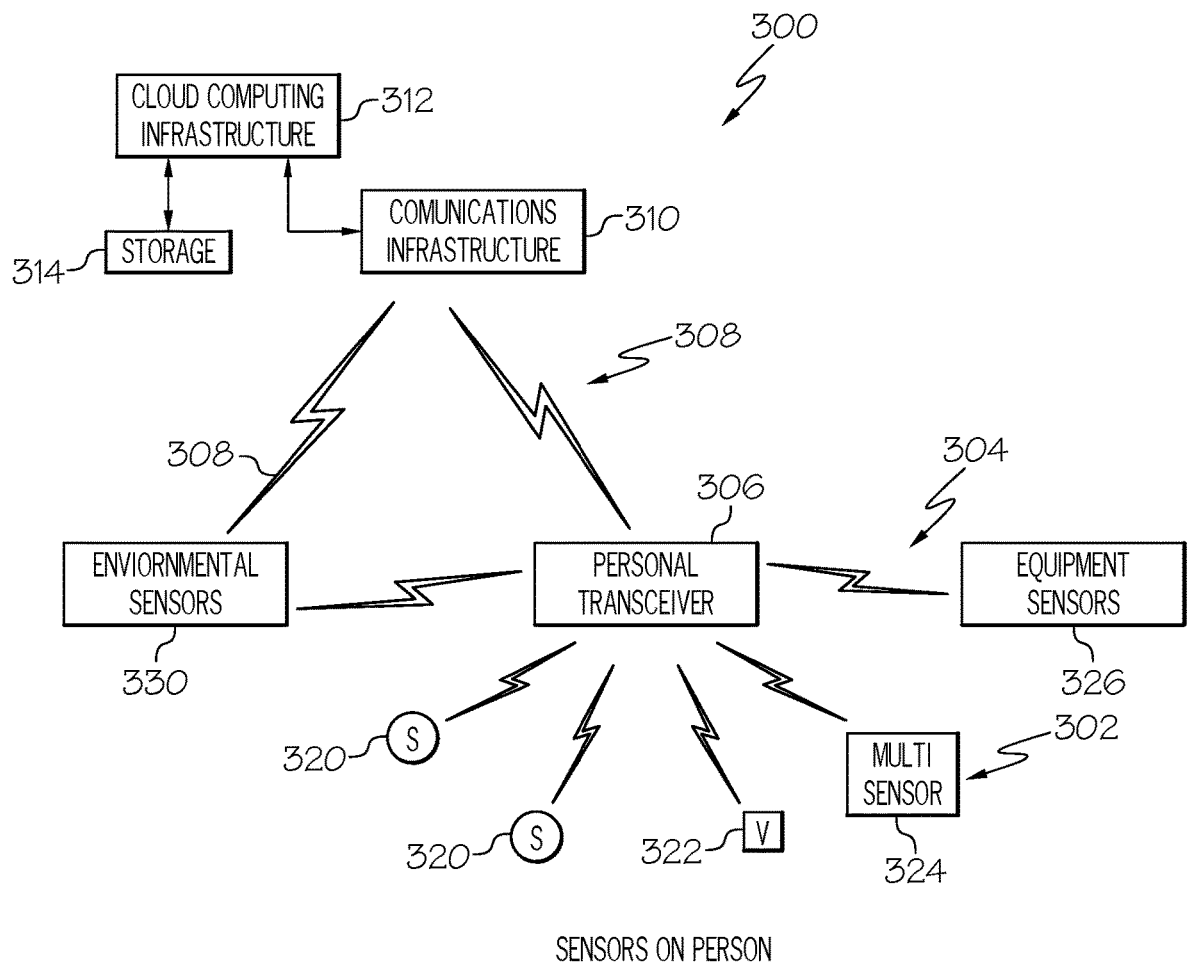
FIG. 3 illustrates a wearable monitoring system interaction diagram, according to an example.

FIG. 3 illustrates a wearable monitoring system interaction diagram 300, according to an example. The wearable monitoring system interaction diagram 300 illustrates the interaction and exchange of data between wearable sensors 302, such as are described above with regards to the wearable sensor placement configuration 200, and other components.

The wearable monitoring system interaction diagram 300 depicts a number of wearable sensors including sensors 320 that are in communications with a personal transceiver 306. The sensors 320 are examples of the sensors 110 depicted in the multiple person monitoring environment 100 and also described above with regards to the wearable sensor placement configuration 200. These sensors 320 are shown in this example to be in wireless communication with the personal transceiver 306 via wireless data links 304. In various examples, the sensors 320 are able to communicate data with the personal transceiver 306 by any wireless technique, such as via data links conforming to Bluetooth®, Near Field Communication, light based communications, other RF communications, other wireless communications, or combinations of these. In other examples, the sensors 320 are able to communicate with the personal transceiver 306 via wired data links.

The wearable monitoring system interaction diagram 300 also depicts a visual sensor 322 that is also in communications with a personal transceiver 306. Examples of a visual sensor 322 are the head mounted visual sensor 260 and the torso mounted visual sensor 270 describe above. The wearable monitoring system interaction diagram 300 further depicts a multi sensor 324 that is also in communications with a personal transceiver 306. The multi sensor 324 is an example of a sensor that is able to sense different quantities and send indications of those quantities to the personal transceiver 306. In an example, the sensors 320, the visual sensor 322, and the multi sensor 324 are able to encrypt data for transmission to the personal transceiver 306.

One or more of sensor 320 or multi sensor 324 is able to determine various quantities related to conditions of the person or related to ambient conditions. For example, such sensors are able to measure pulse rate, blood pressure, $O_2$ levels in the person's blood, any other quantity, or combinations of these.

Equipment sensors 326 are further able to be used in some examples to determine or otherwise derive movements or other characteristics of equipment used by the person. For example, sensors within a ball, bat, medical equipment, other device used by or affected by a person, are able to measure characteristics of affects and effects on that device. Further, equipment sensors 326 in some examples are able to include sensors that are external to the equipment, such as video equipment or other sensors, are able to also characterize usage of some or all of a piece of equipment being used by a person. Such data are provided by equipment sensors 326 is able to be provided to the personal transceiver 306 via any suitable technique, such as a wireless data link 304, and combined with data from other sensors in any suitable manner.

Environmental sensors 330 in some examples measure environmental data near the person and report such data by any technique. For example, environmental data such as air temperature, humidity, other environmental data quantities, or combinations of these, are able to be obtained by the environmental sensors 330. The environmental sensors 330 in some examples are able to communicate with the personal transceiver 306 via a wireless data link 304 and report some or all environmental data to the personal transceiver 306. The personal transceiver 306 is then able to incorporate such environmental data into analyses performed by a processor within the personal transceiver 306, or report the received environmental data with measurements received from other sensors.

In some examples, the personal transceiver 306 is also able to include sensors that determine quantities that can be combined with data indicating quantities determined by sensors worn on the person. For example, sensors determining environmental data at a location proximate to the person, such as measurements including one or more of ambient temperature, humidity, atmospheric pressure, other environmental quantities or conditions, or combinations of these, can be included in the personal transceiver. Additionally, visual sensors such as image capture, video capture, other visual capture capabilities, or combinations of these can be included in the personal transceiver 306. Such personal transceiver mounted visual sensors can be used to, for example, capture images or videos of the person while the person is performing actions of interest, capture images or videos of equipment held or otherwise manipulated or used by the person such as a bat being swung or a ball being thrown, or any other visual information.

The wearable monitoring system interaction diagram 300 illustrates wireless connections between sensors and the personal transceiver 306. In further examples, any suitable communications link is able to be used to convey data between the sensors and the personal transceiver 306. In some further examples, sensors are able to accumulate data and transfer data to any destination over any suitable link, such as over one or more wireless links, wired data links, other links, or combinations of these.

The personal transceiver 306 is able to communicate with a communications infrastructure 310 in order to exchange data with a cloud computing infrastructure 312. In an example, the personal transceiver 306 sends data indicating measured quantities determined by the sensors 320, visual sensor 322, and multi sensor 324 to the cloud computing infrastructure 312. In some examples, the environmental sensors 330 are able to transmit environmental data directly to the communications infrastructure 310 for reporting to the cloud computing infrastructure 312.

The data transmitted from the personal transceiver 306 to the communications infrastructure 310, and on to the cloud computing infrastructure 312, is able to be encrypted. This encryption is able to be performed by various components, such as by the sensor, e.g., sensor 320, visual sensor 322, or multi sensor 324, prior to sending the data to the personal transceiver 306, or the encryption is able to be performed by the personal transceiver 306 prior to transmission. The communications infrastructure 310 in various examples is able to support communications in one or both directions over the wireless data link 308 in any suitable form, such as over wide area cellular data communications networks, over Wi-Fi® networks, over any suitable communications using any combination of wired or wireless networks, or over combinations of these. In further examples, the personal transceiver 306 is able to communicate via a wired communications channel conveying either data that has been accumulated within the personal transceiver 306, data being received or processed within the personal transceiver 306, any data within the personal transceiver 306, or combinations of these.

In some examples, the personal transceiver 306 is able to accumulate measured quantities and other data without transmitting that data until certain criteria are reached. For example, an amount of data may be specified to be accumulated prior to transmission. Further conditions may be specified such that anomalous or data meeting other criteria is reported sooner. Transmitting accumulated data in some examples conserves energy used to transmit the data, while setting other criteria for earlier transmission ensures more interesting data is sent without unnecessary delay.

The personal transceiver 306 in some examples is able to include processing capabilities to perform analysis of measure quantities in order to derive characterizations or other information to provide to the person or to other processors. In some examples, the personal transceiver 306 is able to include a cognitive processor or cognitive computer to analyze data in according to any suitable technique. Examples of cognitive processors or cognitive computers include, but are not limited to, processors that perform processing to implement concepts such as artificial intelligence, machine learning algorithms, or any other suitable techniques. In some examples, the personal transceiver 306 is able to compare measured quantities or derived characteristics to expected values in order to identify anomalous condition. For example, measured data is able to be analyzed to determine if a person has fell, had a heart attack, is undergoing another anomalous situation, or combinations of these. Sending notifications of data that may indicate such conditions notifies others, such as emergency responders, caretakers, others, or combinations of these, of situations that may need attention.

Processing within the cloud computing infrastructure 312 analyses the data received from the personal transceiver 306, and produces results to report to the person associated with the personal transceiver 306. The cloud computing infrastructure 312 is an example of a remote processor to which data is sent from the personal transceiver 306. In some examples, the cloud computing infrastructure 312 is able to include cognitive computers or cognitive processors to perform some functions as is described above. The cloud computing infrastructure 312 is able to store received data indicating measured quantities, store characteristics determined from that received data, store, in association with the data, time points that are associated with that data, store other data, or combinations of these, into a storage 314. The stored data is able to be encrypted in order to, for example, protect the privacy of the person. Alternatively, some or all of the received data, determined characteristics, other data, or any combination of these, are able to be stored in unencrypted form.

Figure 4:
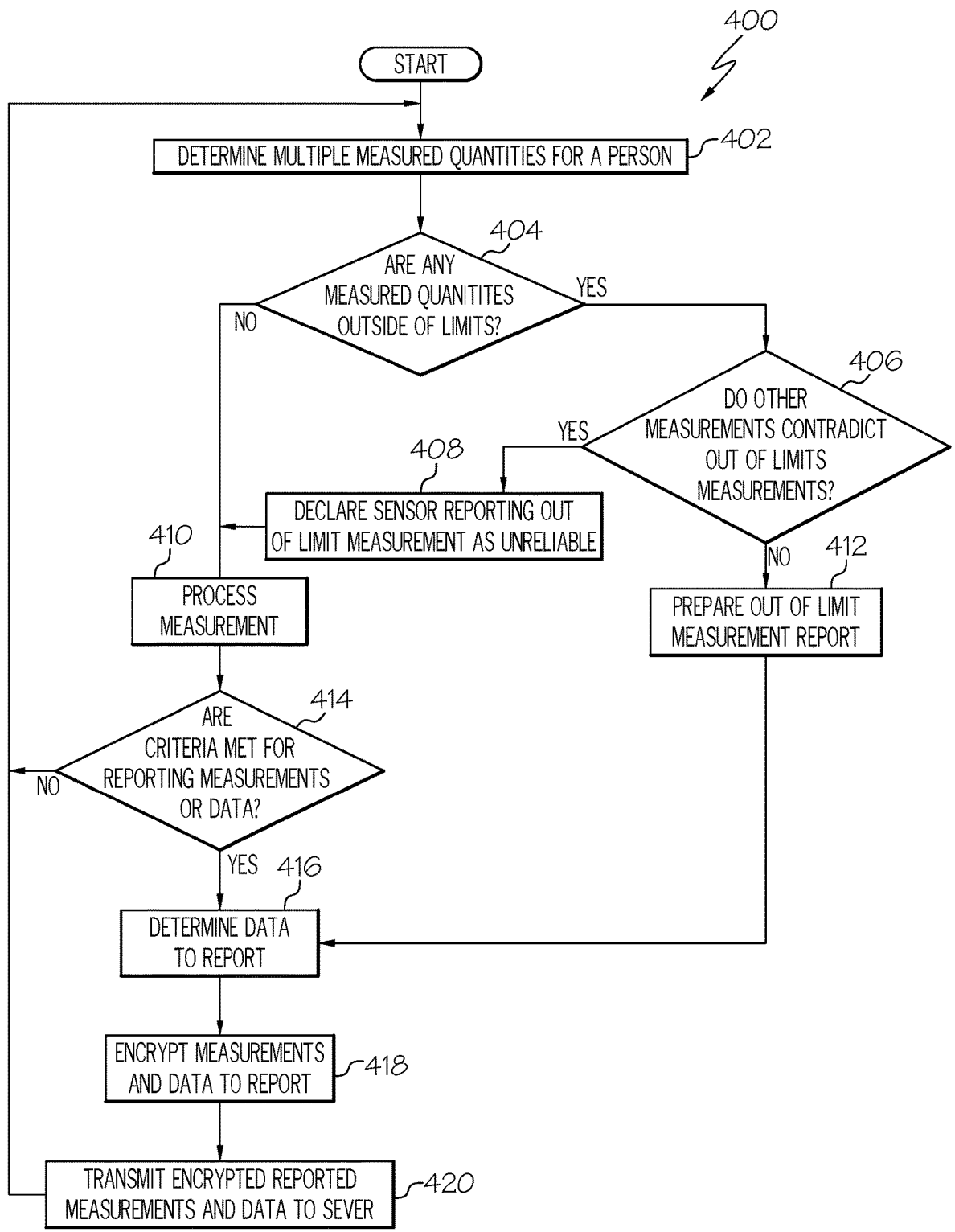
FIG. 4 illustrates a wearable sensor reporting process, according to an example.

FIG. 4 illustrates a wearable sensor reporting process 400, according to an example. The wearable sensor reporting process 400 in one example is performed by a processor within the personal transceiver 306, as is described above, in conjunction with other elements of the wearable monitoring system interaction diagram 300. In further examples, some of this processing is able to be performed by processors within the sensors 320, 322, or 324 themselves prior to reporting measured data to the personal transceiver 306.

The wearable sensor reporting process 400 begins by determining, at 402, multiple measured quantities on a person. As discussed above, determined quantities are able to include quantities for any type of data of that is used in characterizing, analyzing, performing other processing related to, or combinations of these, a person's movements or other type of performance. Various types of sensors are able to be used to determine these quantities, such as are described above with regards to the wearable sensor placement configuration 200 or the sensor 320, visual sensor 322, or multi sensor 324 described above with regards to the wearable monitoring system interaction diagram 300. Such quantities are able to include, for example, location and motion of the sensor, images or videos captured by sensors physically coupled to the person, in the vicinity of the person, or otherwise associated with the person. In an example, determined quantities are able to include images, videos, or other visual captures of the person by a camera mounted near the person. In some examples, an indication of time points, such as the time that the quantities were measured, is also determined and combined with the measured quantities. The determined data is also able to include biometric identification that that is able to be reported, combined with other measured data, or both. Environmental data, such as temperature, humidity, other environmental data, or combinations of these are also able to be determined measured quantities. In some examples, the time of these measurements is determined and associated with the measured quantity. This time of measurement is retained with and sent along with the measured quantity in some examples so as to be available for subsequent processing.

A determination is made, at 404, as to whether any measured quantities are outside limits associated with that quantity. In some examples, limits are able to be set for various quantities measured for a person. In an example, a person's hear rate may be determined or observed to normally be between 60 and 70 beats per minute. When a person's heart rate is in this range, it may be assumed that reporting this quantity is of little benefit to analysis or monitoring since this is a normal condition. In a case where the person's heart rate is below 60 beats per minute or above 70 beats per minute, this is not the normal condition for the person's hear rate and thus this quantity is determined to be reported. In various examples the determination that a quantity is outside of a limit is able to be performed by any element with access to the data. For example, the heart rate sensor itself, such as sensor 320, may be configured to not report heart rates that are within specified limits, or to accumulate those measured quantities and send the an accumulation of data at a later time. Heart rates outside the limits are reported as they are measured in some examples. In further examples, the personal transceiver 306 is able to determine if measured quantities are outside limits and then determine whether to report those quantities.

The determination that a measured quantity is outside of limits is able to be conditioned on other measured quantities. For example, if various sensors on the person indicate that the person is running, such as would be indicated by measured quantities indicating speed and direction of motion of the person's legs, arms, and body, then a higher heart rate may be expected and an upper limit for determining that the rate is outside of limits is able to be raised. Alternatively, a determination that the person is sleeping, such as by analyzing data from sensors measuring breathing rates, body position, etc., the lower heart rate limit may be lowered to accommodate expected heart rates while sleeping.

If any measured quantity is determined to be outside of limits, a determination is made, at 406, as to whether other measured quantities contradict the out of limit measurement. For example, a person may have multiple sensors that measure heart rate. If one sensor indicates no heart rate, while all other sensors measure an expected heart rate or the same heart rate, then the sensor reporting zero heart rate is probably malfunctioning.

If it is determined that other measured quantities contradict the out of limit measurement, the sensor reporting the out of limit measured quantity is declared, at 408, to be unreliable. Marking this sensor as unreliable is able to be used to affect processing of measurements produced by this sensor. For example, measurements from this sensor may not be considered in further processing to determine characteristics in some instances. In further examples, the data may be reported and stored for later analysis, but the measurement's impact on decisions may be reduced to limit the suspect measurements effects on the analysis. In some examples, different limits may be set to determine when a measured quantity is out of limits for purposes of declaring that a sensor is unreliable.

After declaring that a sensor is unreliable, at 408, or after a determination, at 404, that any measured quantities were not outside of limits, the determined measured quantities are processed, at 410. The determined measurements in various examples are able to be subjected to various types of processing within the personal transceiver 306. In further examples, the determined measurements may not be processed within the personal transceiver 306. Processing performed within the personal transceiver 306 by the wearable sensor reporting process 400 is able to include any degree of processing, such as determining trends of measured data, combining measured data to determine recommendations to the user of activities to undertake or to slow down his or her exercise rate, any other processing to support presenting data to the user, any other processing to support reporting measurements to an external server, reducing measurement data for more efficient transmission to a server or other device, any other processing, or combinations of these.

The wearable sensor reporting process 400 determines at 414, if criteria are met for reporting measured quantities or data to a server. Measured quantities in some examples are accumulated prior to being reported to a server in order to conserve data transmission resources, power used to transmit the data, for other reasons, or combinations of these. In some examples, measurements that fall within expected values are accumulated and multiple measurements, or characterizations of multiple measurements, are reported at once. Characterizations of multiple measurements include, for example, and average or other mean value, characterizations of the distribution of values such as variance, moments, any other characterizations, or combinations of these. Accumulating measurements and sending multiple measurement or characterizations of those measurements in some examples allows a reduction in electrical power consumption by reducing the amount or frequency of data transmissions. It is generally more power efficient to send one transmission with more data than to send the same amount of data via multiple transmissions.

In addition to sending measured quantities, other data are able to be reported. For example, data such as environmental data, other data, or combinations of these, are also able to be reported. Additionally, processing of measured quantities, environmental data, other data, or combinations of these are able to produce characterizations related to the person. Any or all of these values are data that is able to be reported. Also, the criteria for reporting any set of data is able to depend on values of one or more of measured quantities, environmental data, other data, or combinations of these. In some examples, different sets of measured quantities are able to be defined that have different criteria for their reporting.

Criteria for which measured quantities or data are to be reported in an example are able to specify an amount of data that is to be accumulated prior to reporting, characteristics of the data, such as data indicating a change in behavior or other activity of the person, other bases, or combinations of these. If it is determined that the criteria for reporting measured quantities are not met, the wearable sensor reporting process 400 returns to determining, at 402, measured quantities for the person and continues with the above described processing.

Returning to determining whether other measured quantities do not contradict the out of limit measured quantity, at 406, when such a contradiction of an out of limit quantity is not determined, an out of limit measurement report is prepared, at 412. In some examples, out of limit measured quantities are reported more quickly than measurements that fall within expected values. In some examples, when a measurement of a certain quantity is outside of a limit, a report for that certain quantity is able to specify other measured quantities or other data to include in a report. For example, if a person's heart rate exceeds a limit, measured quantities that would help determine whether the person is resting or exercising can be specified to be sent in the report.

In some examples, preparing the out of limit measurement report further determines if the out of limit measurement exceeds an alarm trigger point that would indicate an emergency condition that should be notified to the user, another entity such as an emergency service, or both. Alarm trigger points are able to be defined by any suitable technique, such as by one or more of being configured into the algorithm, set based on previously observed values for the person, set by or based on any other criteria, or combinations of these.

Alarm trigger points that indicate emergency conditions are able to be of any nature. In an example, an emergency condition is able to be a personal emergency for the person, such as a sudden heart rate drop to zero, a breath rate drop to zero, other such personal conditions, or combinations of these. In some examples, the emergency condition is able to reflect an environmental condition such as a dangerous level of radiation, toxic gas, or the like. Environmental emergency conditions are able to be determined by, for example, measured environmental quantities that are determined to be outside of limits. In some examples, an environmental emergency condition is able to be reported as described below. In further examples, emergency conditions are able to be notified to the person as a warning through a device close to the user. In some examples, the out of limit measurement report prepared for out of limit measurements corresponding to emergency conditions are able to be sent as an alarm to remote processor. In some examples, the remote processor is able to send an alarm notification to the user based on its processing of data. In some examples, an interactive personal verification mechanism is also able to be incorporated in order to limit possible false alarms.

After preparing an out of limit measurement report, at 412, or after determining that criteria are met for reporting measurements, at 414, the wearable sensor reporting process 400 determines, at 416, data to report. Various conditions defining which data is to be reported are able to be defined. For example, all measured data is able to be reported with less frequency that certain types of measured data. In various examples, a time associated with the measurement of measured data is included in the report.

Data indicating the measured quantities, other data, or combinations of these, that are to reported are then encrypted in one example, at 418. This encryption is able to be performed in various examples at other stages of the process, such as by the sensor determining the measured quantity, or this encryption is able to be performed after the quantity is measured by another component, such as the personal transceiver 306 described above. In some alternative examples, the data is able to not be encrypted at this stage or in further examples at any stage.

The encrypted data in one example is transmitted, at 420, to a cloud computing infrastructure. In an example, with reference to the wearable monitoring system interaction diagram 300 described above, the personal transceiver 306 transmits the encrypted data via a wireless data link 308 to a communications infrastructure 310. Transmission over the wireless data link 308 is able to be in any suitable form, such as over a wide area cellular data communications network, over a Wi-Fi® network, over any suitable wireless network, or over combinations of these. In alternative examples, encrypted or unencrypted data is able to be transmitted to any remote server, such as a server in a cloud based infrastructure, over any suitable channel that includes only wired connections, only wireless connections, or any combination of wired and wireless connections. The wearable sensor reporting process 400 then returns to determining, at 402, measured quantities for the person and continues with the above described processing.

Figure 5:
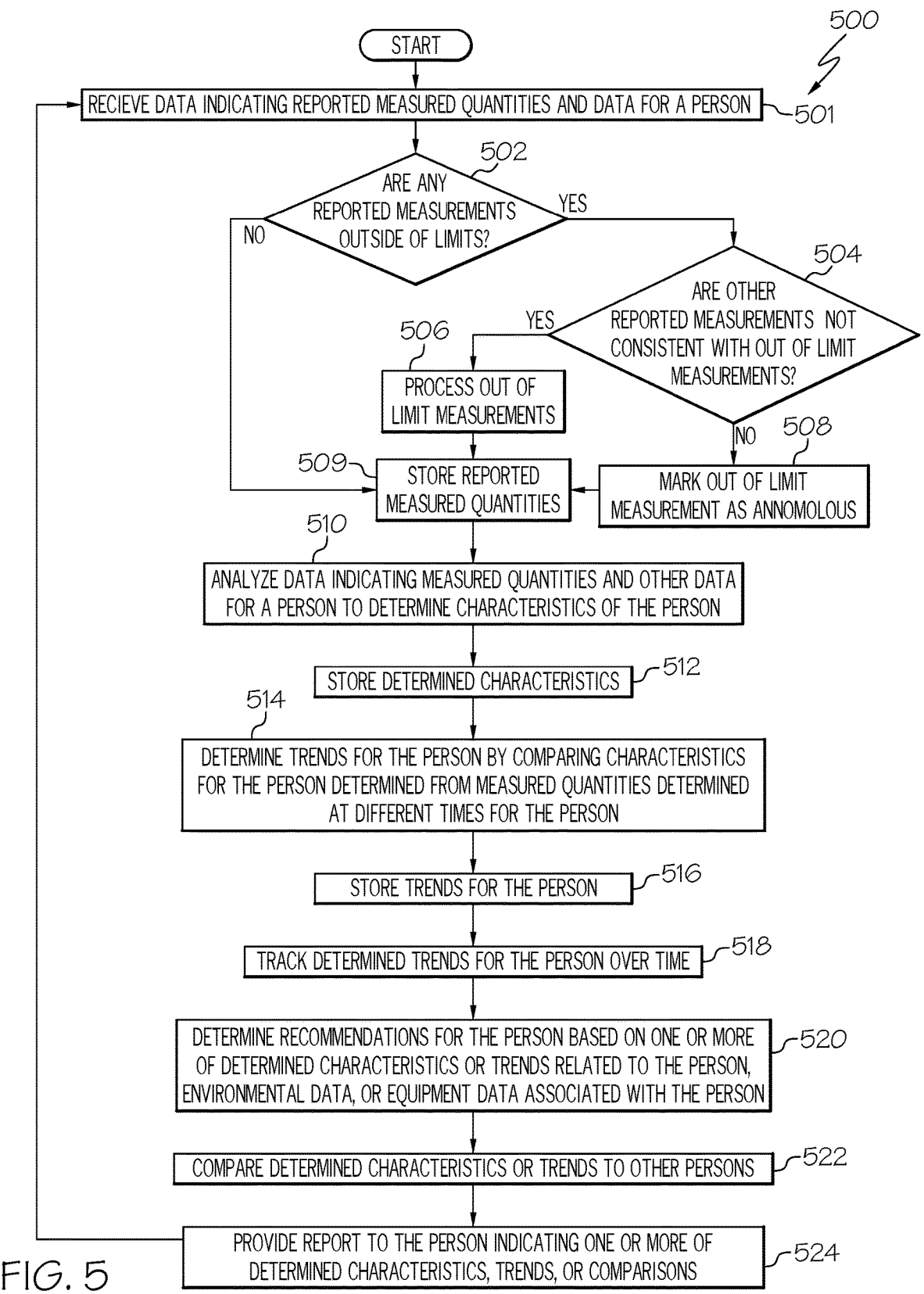
FIG. 5 illustrates a reported measured data analysis process, according to an example.

FIG. 5 illustrates a reported measured data analysis process 500, according to an example. The reported measured data analysis process 500 in one example is performed by a processor located in a server or in a cloud computing infrastructure. In general, the reported measured data analysis process 500 receives reported measured quantities from the personal transceiver 306 and processes or otherwise operates on the received quantities to produce various results to provide the person, a health or physical fitness professional working with the person, any authorized person, or combinations of these.

The reported measured data analysis process 500 receives, at 501, reported measured quantities and data for a person. The received measured quantities and data for a person are able to be received from any source. For example, measured quantities and data are able to be received from a personal transceiver 306 as is discussed above. Additional measured quantities and data for the person are able to be received from other sources, such as environmental data at a point proximate to the person and associated with the time point of measured quantities. Such environmental data is able to include temperature, humidity, other environmental data, or combinations of these; that are obtained through any source sufficiently close to the person that it is expected to represent the environment at the person's location. Other data is able to include video data such as videos of the person's movements; other data measured or collected by any technique; or combinations of these. The received measured quantities and data is able to include any information that is sent, including measured quantities, characterizations determined by processing the measured quantities, other data, times associated with measured quantities or other data, or combinations of these. The received measured quantities and data are able to also include indications of a time point for any or all of the measured quantities or data being communicated. In general, the time point associated with a measured quantity or other data is a time that pertains to that measured quantity or data, such as the time when the quantity was measured or the data was or is valid. The received measured quantities and data in some examples include data that is encrypted.

In an example, with reference to the wearable monitoring system interaction diagram 300 described above, the personal transceiver 306 transmits the encrypted data via a wireless data link 308 to a communications infrastructure 310 and on to a cloud based computing infrastructure. Reception of data conveying these measured quantities and data is able to include receiving data transmitted over a wireless data link 308, other channels, or combinations of these. This data is able to be received in any suitable form corresponding to the form in which it is transmitted. Examples of data communications through which the reported measured data analysis process 500 is able to receive data include, but are not limited to, wide area cellular data communications networks, Wi-Fi® networks, over any suitable wireless network or networks, or over combinations of these. In alternative examples, encrypted or unencrypted data is able to be received by the reported measured data analysis process 500 operating on any remote server, such as a server in a cloud based infrastructure, over any suitable channel that includes only wired connections, only wireless connections, or any combination of wired and wireless connections.

The reported measured data analysis process 500 determines, at 502, if any reported measurements are outside of limits. Limits for reported data are able to be defined based on any criteria, such as limits of safe values for quantities such as heart rage, body temperature, hydration level, and the like. Measured quantities that are outside of limits are able to be accurate measurements of the quantity. In some instances, a sensor may report an anomalous measurement due to a malfunction, communications failure, other causes, or combination of these.

If it is determined that any reported measured quantity is outside a limit, a determination is made, at 504, as to whether other reported measurements are consistent with that out of limit measurement. If it is determined that other reported measurements are not consistent with this the out of limit measurement, the out of limit measurement is marked as anomalous, at 508. In various examples, the measurements are able to be marked as anomalous or the sensor that made the measurement is able to be marked as suspect or unreliable.

Returning to determining, at 504, if the other reported measurements are consistent with the out of limits measurement, the reported measured data analysis process 500 processes, at 506, the out of limit data. In various examples, out of limit data may indicate a problem with the person and alerts of the problem are able to be sent to caretakers or others. For example, measured quantities may indicate the person is suffering a heart attack, and emergency responders may be notified. In an example of a person recovering from knee surgery, a temperature sensor on the person's knee may indicate a rise in body temperature at the location of surgery, which could indicate an infection. A notification could be sent in that case to the person or caregiver indicating that an infection of that location is suspected. In some examples, alarm limit points such as are described above are able to be implemented in the reported measured data analysis process to control notifying various entities, such as the person himself or herself, emergency responders, other entities, or combinations of these.

The received reported measured quantities and data are stored, at 509. The stored measured quantities and data are also able to have an associated time point stored with them to indicate the time point associated with the measured quantity or data. Storage of these measured quantities and data allows subsequent processing to analyze the data, determine trends in the data, perform other processing and analysis, or support other operations. The measured quantities and data are able to be stored in any suitable facility. Stored measured quantities and data are able to be encrypted and/or otherwise protected to ensure against unauthorized disclosures. In general, access to stored data about a person, such as reported measurements, processed data, determined characteristics, other data, or combinations of these, is able to be restricted by any suitable technique. The data is able to be stored in any suitable equipment or facility that is located in proximity to a server that receives the data, any data storage accessible through a cloud based infrastructure, any other suitable storage, or combinations of these.

The data indicating the measured quantities and other data for a person is analyzed, at 510, to determine characteristics of the person. Examples of analysis that is able to be included as part of the reported measured data analysis process 500 are able to include combining measurements of the person to determine characteristics such as fatigue, dehydration level, wind speed, conditions under which the person does well, determine when the person is having a good day or bad day for things such as speed or endurance. Other characteristics is able to include determining heart rate, running impact on road, legs or bones, weight over time versus loss of fluids, body levels of glucose, temperature, and the like. In some examples, environmental data, equipment data, other data related to the person's activities, or any other data, is also able to be included in the data analysis at this stage.

These determined characteristics are stored, at 512. These characteristics that are determined by analysis of the measured quantities associated with the person are able to be stored in any suitable location and equipment. For example, these determined characteristics are able to be stored in conjunction with the data indicating the measured quantities, are able to be stored separately, stored in any combination with other data, or combinations of these. These determined characteristics are able to be stored in an encrypted form, an unencrypted form, a combination of partially encrypted or unencrypted form, or combinations of these.

Trends for the person are determined, at 514, by comparing different sets of characteristics for the person. In an example, these different set of characteristics are determined by analyzing measured quantities that were determined at different times. In an example, these different sets of determined characteristics form a time progression of characteristics for the individual. One or more trends in characteristics, such as increasing speed or strength, improvement in form or agility, other developments associated with the person, or combinations of these, are able to be determined to support analysis of the person's development and, for example, to assist in formulating recommendations for changes or additions to the person's exercise, training, other routines, any other activities, or combinations of these.

The determined trends are stored, at 516. These trends are able to be stored in any suitable location and equipment. For example, these determined characteristics are able to be stored in conjunction with the data indicating the measured quantities, stored in conjunction with the data indicating the determined characteristics, are able to be stored separately, stored in any combination with other data, or combinations of these. The determined trend data is able to be stored in an encrypted form, an unencrypted form, a combination of partially encrypted or unencrypted form, or combinations of these.

Determined trends for the person are tracked, at 518, over time. Tracking trends is able to support, for example, more extensive evaluation of the person's development or other improvements or changes, based on quantities measured during the individual's activities over a period of time.

Recommendations for the person are determined, at 520, based on one or more of measured quantities, determined characteristics, determined trends, environmental data, equipment data, any combinations of these in conjunction with any other available data, or any combination these. Environmental data and equipment data associated with the person is able to include any data indicating environmental conditions or any characterization associated with equipment used by the person, respectively. Such recommendations are a form of feedback to be provided to the individual.

Such recommendations are able to include modifications, curtailment, additions, or other changes to one or more routines followed by the individual. Recommendations may be determined for modifications to training or rehabilitation routines to improve, for example, performance in sports such as running, golf, tennis, etc., healthcare, wellness surgery recovery, or improving ones condition with respect to conditions for receiving various types of insurance. In some examples, determination of these recommendations is able to include analysis by professionals such as doctors, health care professionals, wellness professionals, others knowledgeable in developing routines to achieve desired results, or combinations of these.

In addition to, or in place of, determining and providing recommendations based on measured and determined data, some examples compare, at 522, the measured quantities, determined characteristics, determined trends, or combinations of some or all of these, between the individual for whom measured quantities were received and other individuals whose data is available by various techniques. For example, an individual's data associated with measured quantities, determined characteristics, determined trends, or combinations of some or all of these, can be compared to the same or corresponding data for professional athletes, the individual's trainer, other persons, or combinations of these.

A report indicating one or more of determined characteristics, trends, comparisons of the person's data to other person's or combinations are provided, at 524. This report is able to be provided by any suitable technique. A report is able to be prepared and stored in the cloud based infrastructure 312 and that report is able to be accessed at any time. In some examples, the report is stored in encrypted form. In some examples, access to a report for a particular individual is restricted to that individual or persons authorized by that individual to access that report. In some examples, the report, a summary of the report, various representations of information in the report, other information, or combinations of these is able to be provided to the person by sending such information from the cloud based infrastructure 312, or other processing resource creating or storing the report, via the communications infrastructure 310 and wireless data link 308 to the personal transceiver 306. In one such example, the personal transceiver is a smartphone that is able to securely receive and store the report, and restrict access to the report by various authentication techniques on the device. In some examples, access to the report on various devices is able to be controlled by authentication based on, for example, passwords, biometric authentication techniques, any other authentication techniques, or combinations of these. The reported measured data analysis process 500 then returns to receiving, at 501, multiple data indicating reported measurements of a person, and continues with the above described processing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
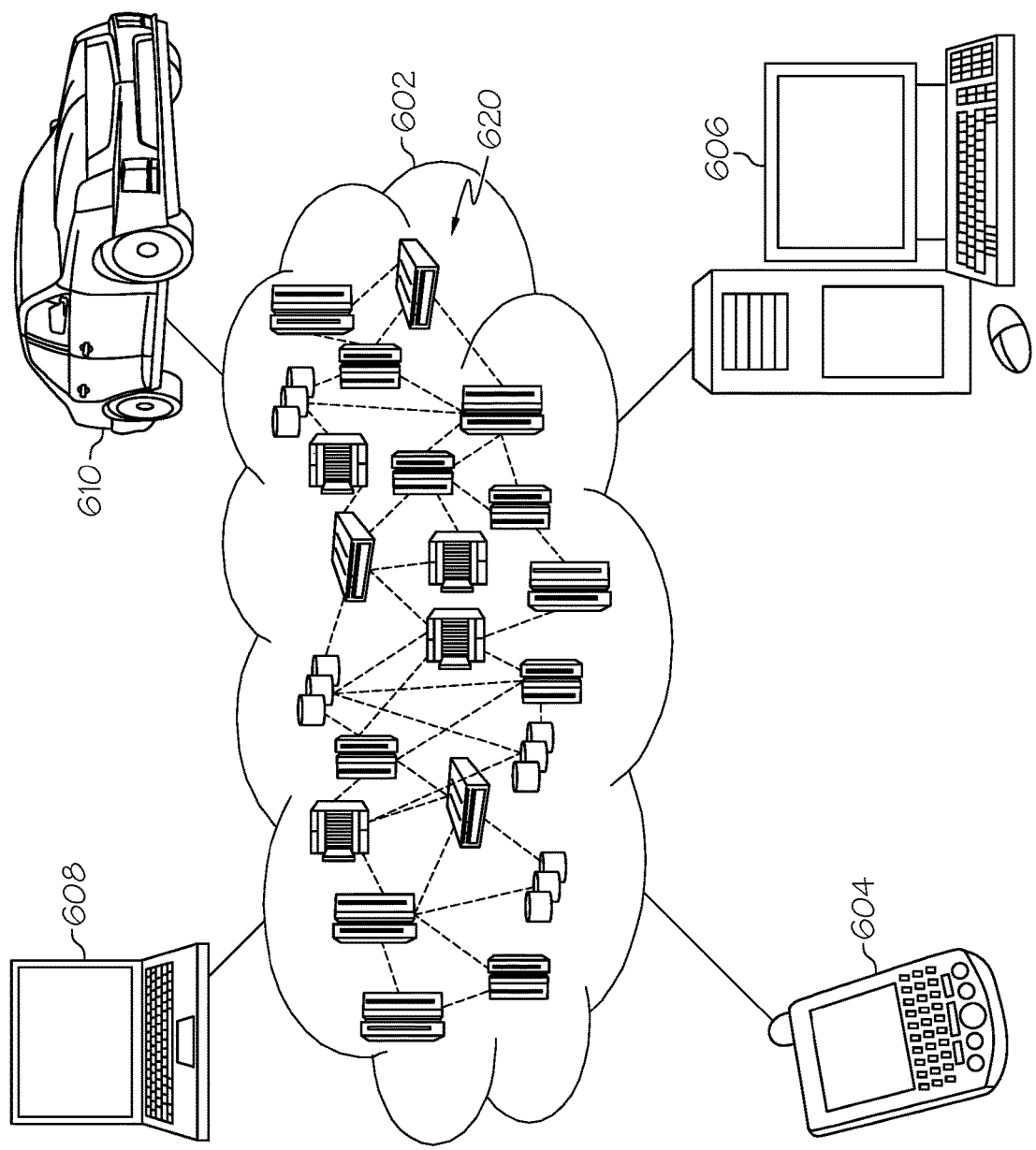
FIG. 6 depicts a cloud computing environment according to an embodiment of the present invention.

Referring now to FIG. 6, illustrative cloud computing environment 602 is depicted. As shown, cloud computing environment 602 comprises one or more cloud computing nodes 620 with which local computing devices used by cloud consumers, such as, for example, personal digital assistant (PDA) or cellular telephone 604, desktop computer 606, laptop computer 608, and/or automobile computer system 610 may communicate. Nodes 620 may communicate with one another. They may be grouped (not shown) physically or virtually, in one or more networks, such as Private, Community, Public, or Hybrid clouds as described hereinabove, or a combination thereof. This allows cloud computing environment 602 to offer infrastructure, platforms and/or software as services for which a cloud consumer does not need to maintain resources on a local computing device. It is understood that the types of computing devices 604-810 shown in FIG. 1 are intended to be illustrative only and that computing nodes 620 and cloud computing environment 602 can communicate with any type of computerized device over any type of network and/or network addressable connection (e.g., using a web browser).

Figure 7:
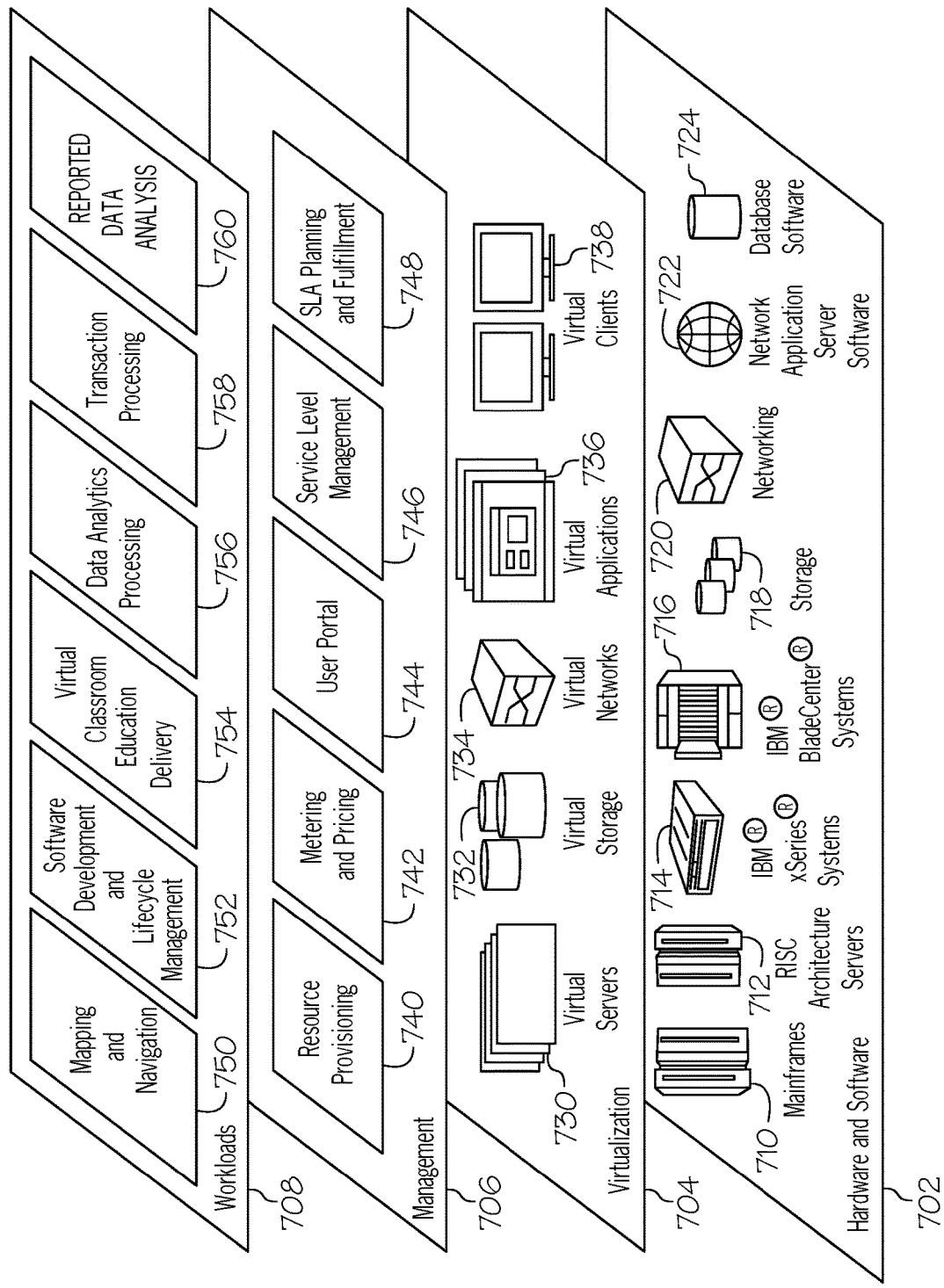
FIG. 7 depicts abstraction model layers according to an embodiment of the present invention.

Referring now to FIG. 7, a set of functional abstraction layers provided by cloud computing environment 602 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 702 includes hardware and software components. Examples of hardware components include: mainframes 710; RISC (Reduced Instruction Set Computer) architecture based servers 712; servers 714; blade servers 716; storage devices 718; and networks and networking components 720. In some embodiments, software components include network application server software 722 and database software 724.

Virtualization layer 704 provides an abstraction layer from which the following examples of virtual entities may be provided: virtual servers 730; virtual storage 732; virtual networks 734, including virtual private networks; virtual applications and operating systems 736; and virtual clients 738.

In one example, management layer 706 may provide the functions described below. Resource provisioning 740 provides dynamic procurement of computing resources and other resources that are utilized to perform tasks within the cloud computing environment. Metering and Pricing 742 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 744 provides access to the cloud computing environment for consumers and system administrators. Service level management 746 provides cloud computing resource allocation and management such that required service levels are met. Service Level Agreement (SLA) planning and fulfillment 748 provide pre-arrangement for, and procurement of, cloud computing resources for which a future requirement is anticipated in accordance with an SLA.

Workloads layer 708 provides examples of functionality for which the cloud computing environment may be utilized. Examples of workloads and functions which may be provided from this layer include: mapping and navigation 750; software development and lifecycle management 752; virtual classroom education delivery 754; data analytics processing 756; transaction processing 758; and reported data analysis 760.

Information Processing System

Figure 8:
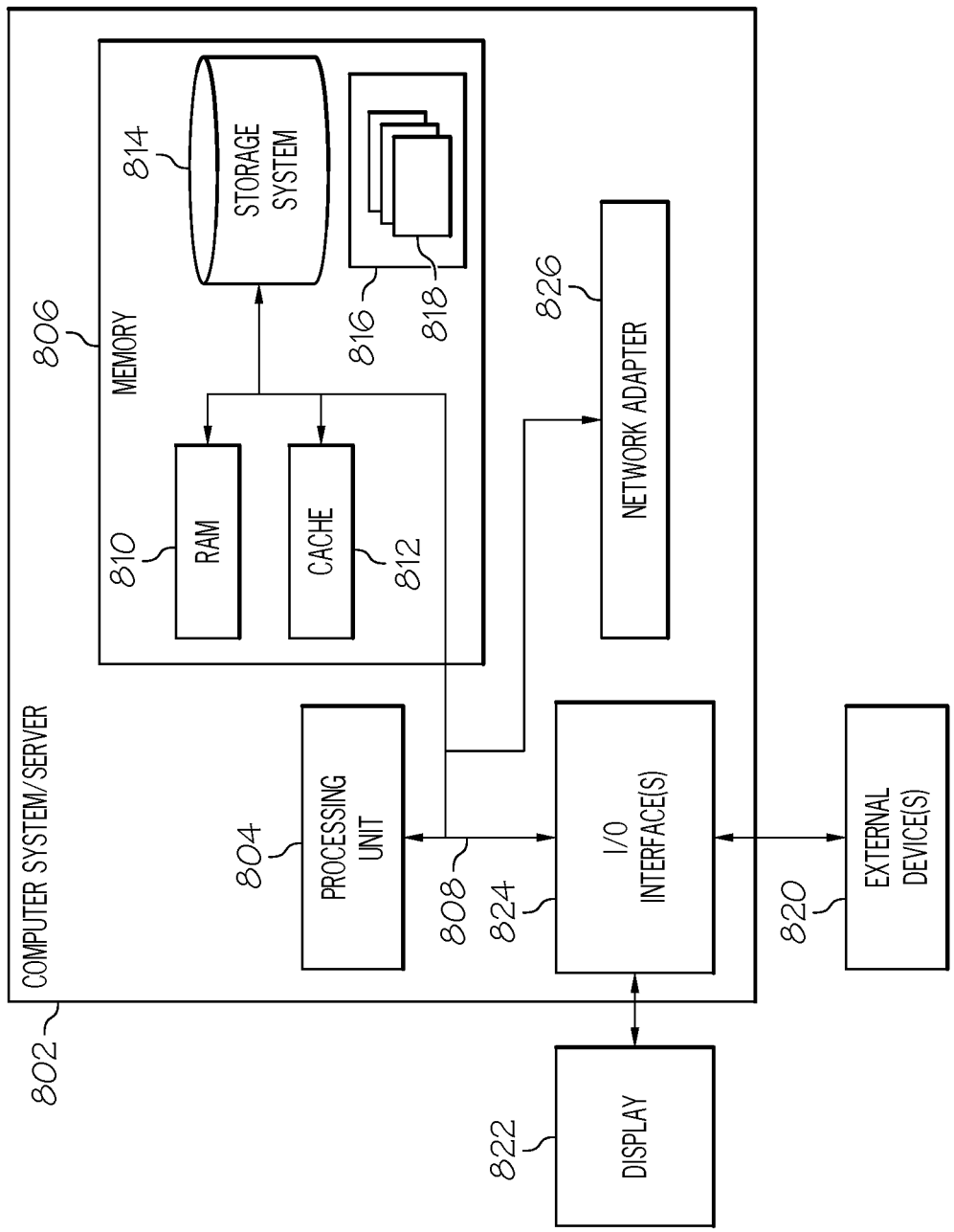
FIG. 8 is a block diagram illustrating one example of an information processing system according to one example.

Referring now to FIG. 8, this figure is a block diagram illustrating an information processing system that can be utilized in various examples of the present disclosure. The information processing system 802 is based upon a suitably configured processing system configured to implement one or more embodiments of the present disclosure. Any suitably configured processing system can be used as the information processing system 802 in embodiments of the present disclosure. In another embodiment, the information processing system 802 is a special purpose information processing system configured to perform one or more embodiments discussed above. The components of the information processing system 802 can include, but are not limited to, one or more processors or processing units 804, a system memory 806, and a bus 808 that couples various system components including the system memory 806 to the processor 804.

The bus 808 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 806 can also include computer system readable media in the form of volatile memory, such as random access memory (RAM) 810 and/or cache memory 812. The information processing system 802 can further include other removable/non-removable, volatile/non-volatile computer system storage media. By way of example only, a storage system 814 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 808 by one or more data media interfaces. The memory 806 can include at least one program product having a set of program modules that are configured to carry out the functions of various examples described above.

Program/utility 816, having a set of program modules 818, may be stored in memory 806 by way of example, and not limitation, as well as an operating system, one or more application programs, other program modules, and program data. Each of the operating system, one or more application programs, other program modules, and program data or some combination thereof, may include an implementation of a networking environment. Program modules 818 generally carry out the functions and/or methodologies of the above described processes and systems.

The information processing system 802 can also communicate with one or more external devices 820 such as a keyboard, a pointing device, a display 822, and the like. The information processing system 802 is further able to communicate with one or more devices that enable a user to interact with the information processing system 802; and/or any devices (e.g., network card, modem, etc.) that enable computer system/server 802 to communicate with one or more other computing devices. Such communication can occur via I/O interfaces 824. Still yet, the information processing system 802 can communicate with one or more networks such as a local area network (LAN), a general wide area network (WAN), and/or a public network (e.g., the Internet) via network adapter 826. As depicted, the network adapter 826 communicates with the other components of information processing system 802 via the bus 808. Other hardware and/or software components can also be used in conjunction with the information processing system 802. Examples include, but are not limited to: microcode, device drivers, redundant processing units, external disk drive arrays, RAID systems, tape drives, and data archival storage systems.

Non-Limiting Examples

As will be appreciated by one skilled in the art, aspects of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), a phase change memory (PCM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method on a processor, the method comprising:
    receiving data indicating a plurality of measured quantities associated with movement of respective parts of a person at a time point, each respective measured quantity within the plurality of measured quantities having been determined by a respective sensor physically coupled to a respective part of the person at a respective location on the person;
    receiving environmental data indicting environmental quantities associated with the person;

determining at least one characteristic of the person associated with the time point based on analyzing the plurality of measured quantities in combination with the environmental data;

storing the at least one characteristic;

determining at least one recommendation for the person based upon the characteristics;

providing a report comprising the at least one recommendation;

comparing each respective measured quantity with respective expected values for respective movements of the respective part of the person at the respective location to which the respective sensor is coupled;

defining respective alarm trigger points corresponding to the respective expected values for respective movements of the respective part of the person;

comparing the respective measured quantity with a respective alarm trigger point;

determining, based on comparing the respective measured quantities with expected values and on comparing the respective measured quantity with a respective alarm trigger point, an anomalous condition for the person, the anomalous condition corresponding to an emergency condition with the person; and notifying, based on determining the anomalous condition for the person, an emergency responder of the emergency condition of the person.

2. The method of claim 1, further comprising receiving equipment data indicating usage of at least one piece of equipment being used by the person at the time point, and wherein determining the at least one recommendation for the person is further based on the equipment data.

3. The method of claim 1, further comprising:

receiving equipment data indicating usage of at least one piece of equipment being used by the person at the time point, wherein determining the at least one characteristic is further based on analyzing the equipment data with the plurality of measured quantities.

4. The method of claim 1, further comprising:

storing the at least one characteristic in association with an indication of the time point;

determining at least one subsequent characteristic associated with the person at a subsequent time point that is subsequent to the time point, the at least one subsequent characteristic being determined based upon analysis of a subsequent plurality of measured characteristics; and determining a trend for the person based on the at least one characteristic and the at least one subsequent characteristic.

5. The method of claim 4, further comprising determining, based on the trend, recommendations for the person.

6. The method of claim 1, further comprising:

receiving, in association with the data indicating the plurality of measured quantities, biometric identification data associated with the person;

storing, in association with the data indicating the plurality of measured quantities, the biometric identification data associated with the person; and limiting access to a storage storing the at least one characteristic or the data indicating the plurality of measured quantities based on a verification, in association with the access, of biometric identification data.

7. The method of claim 1, further comprising providing the at least one recommendation to at least one of a healthcare professional, a coach, a doctor or a designated receiver of information associated with the person.

8. The method of claim 1, further comprising:

determining, based on comparing the respective measured quantities with expected values, that a first measured quantity within the plurality of measured quantities exceeds a respective alarm trigger point for the first measured quantity; and determining, based on determining that the first measured quantity exceeds a respective alarm trigger point for the first measured quantity, whether at least one other measured quantity contradicts the first measured quantity, where determining the an anomalous condition for the person is further based on determining that the at least one other measured quantity contradicts the first measured quantity.

9. A data processor, comprising:

a data receiver that, when operating:

receives data indicating a plurality of measured quantities associated with movement of respective parts of a person at a time point, each respective measured quantity within the plurality of measured quantities having been determined by a respective sensor physically coupled to a respective part of the person at a respective location on the person; and receives environmental data indicting environmental quantities associated with the person; and a data analyzer that when operating:

determines at least one characteristic of the person associated with the time point based on analyzing the plurality of measured quantities in combination with the environmental data;

stores the at least one characteristic;

determines at least one recommendation for the person based upon the characteristics;

provides a report comprising the at least one recommendation;

compares each respective measured quantity with respective expected values for respective movements of the respective part of the person at the respective location to which the respective sensor is coupled;

defines respective alarm trigger points corresponding to the respective expected values for respective movements of the respective part of the person;

compares the respective measured quantity with a respective alarm trigger point;

determines, based on comparing the respective measured quantities with expected values and on comparing the respective measured quantity with a respective alarm trigger point, an anomalous condition for the person, the anomalous condition corresponding to an emergency condition with the person; and notifies, based on determining the anomalous condition for the person, an emergency responder of the emergency condition of the person.

10. The data processor of claim 9, wherein the data receiver, when operating, further:

receives data comprises receiving encrypted data comprising the data indicating a plurality of measured quantities associated with movement of a person; and decrypts the encrypted data.

11. The data processor of claim 9, wherein the data receiver, when operating, further receives equipment data indicating usage of at least one piece of equipment being used by the person at the time point, and wherein the data analyzer determines the at least one recommendation for the person based on the equipment data.

12. The data processor of claim 9, wherein the data analyzer, when operating, further determines the at least one recommendation based on at least one of:
   one or more measured quantities within the plurality of measured quantities associated with movement of a person at a time point;
   environmental data associated with the time point at a location proximate to the person in combination with the one or more measured quantities;
   equipment data associated with the time point at a location proximate to the person in combination with the one or more measured quantities; and
   trend data determined for the person based on a plurality of one or more measured quantities observed at different times.

13. The data processor of claim 9, wherein the receiver, when operating, further:
   receives environmental data associated with the time point and a location proximate to the movement, and
   wherein the data analyzer, when operating, determines the at least one characteristic further based on analysis of the environmental data with the plurality of measured quantities.

14. The data processor of claim 9, further comprising:
   a data storage that when operating stores the at least one characteristic in association with an indication of the time point, and wherein the data analyzer, when operating, further:
   determines at least one subsequent characteristic associated with the person at a subsequent time point that is subsequent to the time point, the at least one subsequent characteristic being determined based upon analysis of a subsequent plurality of measured characteristics; and
   determines a trend for the person based on the at least one characteristic and the at least one subsequent characteristic.

15. The data processor of claim 14, wherein the data analyzer, when operating, further determines, based on the trend, recommendations for the person.

16. The data processor of claim 9, wherein the receiver, when operating, further receives, in association with the data indicating the plurality of measured quantities, biometric identification data associated with the person, and the data processor further comprising:
   a data storage that, when operating:
   stores, in association with the data indicating the plurality of measured quantities, the biometric identification data associated with the person; and
   limits access to a storage storing the at least one characteristic or the data indicating the plurality of measured quantities based on a verification, in association with the access, of biometric identification data.

* * * * *